United States Patent [19]
Pena

[11] Patent Number: 5,225,189
[45] Date of Patent: Jul. 6, 1993

[54] MINOXIDIL GEL

[75] Inventor: Lorraine E. Pena, Kalamazoo, Mich.

[73] Assignee: The Upjohn Company, Kalamazoo, Mich.

[21] Appl. No.: 566,438

[22] PCT Filed: Feb. 18, 1988

[86] PCT No.: PCT/US88/00403

§ 371 Date: Aug. 17, 1990

§ 102(e) Date: Aug. 17, 1990

[51] Int. Cl.$^5$ .................. A61K 7/06; A61K 31/505
[52] U.S. Cl. .................................. 424/70; 424/78.02; 514/929
[58] Field of Search ............... 424/484, 487, 59, 70, 424/71, 78, 72; 514/880, 929

[56] References Cited

U.S. PATENT DOCUMENTS 4,139,619  2/1979  Chidsey, III ..................... 424/45
4,478,853  10/1984  Chaussee ......................... 424/358

FOREIGN PATENT DOCUMENTS

0104037A1  3/1984  European Pat. Off. .
0188791A1  7/1986  European Pat. Off. .
2602424  2/1918  France .
2590897  6/1987  France .
2023000A  12/1979  United Kingdom .

OTHER PUBLICATIONS

Allen, L. V. and M. L. Stiles, "Compounder's Corner", The Missouri Pharmacist, p. 35 (Jan. 1987).

Primary Examiner—Thurman K. Page
Assistant Examiner—Neil Levy
Attorney, Agent, or Firm—Lawrence T. Welch

[57] ABSTRACT

The present invention provides a novel pharmaceutically acceptable gel containing minoxidil for topical application.

9 Claims, No Drawings

MINOXIDIL GEL

BACKGROUND OF THE INVENTION

The present invention relates to a novel composition of matter. More particularly, the present invention relates to a topical gel for the administration of minoxidil. The chemical name for minoxidil is 2,4-diamino-6-piperidinylpyrimidine-3-oxide and is the active ingredient of Loniten® tablets which are marketed by the Upjohn Company for hypertension. See, Physician's Desk Reference, 38th Edition, page 2033 (1984). The preparation and antihypertensive use of this compound is described in U.S. Pat. No. 3,461,461. This compound is also useful when applied topically to grow hair as described and claimed in U.S. Pat. No. 4,139,619.

INFORMATION DISCLOSURE

The prior known topical pharmaceutical compositions of minoxidil are disclosed in U.S. Pat. No. 4,139,619. This patent describes topical compositions comprising minoxidil and a topical pharmaceutical carrier selected from the group consisting of ointments, lotions, pastes, jellies, sprays, and aerosols. In addition, pharmacies in the U.S. have made and sold gels of topical minoxidil containing carbomer, propylene glycol, and rubbing alcohol. Similarly, the pharmacists' column "Compounder's Corner", printed in, e.g., "The Missouri Pharmacist", page 35, (January 1987) suggests the preparation of a minoxidil gel containing carbopol, ethanol, and water. Neither of these latter formulations are believed to be pharmaceutically elegant.

SUMMARY OF THE INVENTION

The present invention particularly provides:

(1) a pharmaceutically acceptable gel composition comprising the following components on a percent weight to weight basis (% w/w)

| Component | % weight to weight |
| --- | --- |
| (a) water | q.s. 100 |
| (b) carbomer | 0.25–1.5 |
| (c) minoxidil | 0.001–3 |
| (d) pharmaceutically acceptable glycol | 0.01–30 |
| (e) ethanol or isopropanol | 20–40 |
| (f) a water and alcohol soluble amine | 0.25–1.5 | with the proviso that the ratio of minoxidil to the glycol is sufficient for a saturated solution of minoxidil;

(2) a process for preparing a minoxidil gel comprising
 (a) preparing the 3 mixtures or parts, each part containing components in the specified ranges, calculated on the basis of the final gel composition, expressed as percent weight-to-weight:

| | | % w/w |
| --- | --- | --- |
| | Part I | |
| (i) | water | q.s. 100 |
| (ii) | carbomer | 0.25–1.5 |
| | Part II | |
| (iii) | minoxidil | 0.001–3 |
| (iv) | a pharmaceutically acceptable glycol | 0.01–30 |
| (v) | ethanol or isopropanol | 12.9–30 |
| (vi) | a water and alcohol soluble amine | 0.25–1.5 | wherein the ratio of the minoxidil to the propylene glycol is sufficient for a saturated solution of minoxidil;

| | | % w/w |
| --- | --- | --- |
| | Part III | |
| (vii) | ethanol or isopropanol | 27.1–15 |
| (viii) | a water and alcohol soluble amine | 0–0.4 |

(b) adding Part III to Part I and mixing; and subsequently,
 (c) adding Part II to the mixture of Parts III and I and mixing until a uniform gel is obtained.

The present invention thus provides a novel, pharmaceutically elegant means to topically administer minoxidil.

Pharmaceutically acceptable gels of minoxidil have not been previously described in any reference of which the inventor is aware.

Gels are semisolid systems consisting of either suspensions made up of small inorganic particles or large organic molecules interpenetrated by a liquid. Single-phase gels, as used herein, consist of organic macromolecules uniformly distributed throughout a liquid in such a manner that no apparent boundaries exist between the dispersed macromolecules and the liquid. Single-phase gels may be made from synthetic macromolecules (e.g., Carbomer) or from natural gums (e.g. Tragacanth).

The instantly claimed gel is a single phase gel made from a class of synthetic macromolecules called carbomers. A carbomer is a synthetic, high molecular weight, cross linked polymer of acrylic acid. Preferred for use in the instant invention is Carbopol® 934P, a pharmaceutical grade commercial product sold by B. F. Goodrich Company. Carbopol® 934P has an approximate molecular weight of $3 \times 10^6$. Carbomers are well known to those of ordinary skill in the pharmaceutical art.

Attempts to form pharmaceutically elegant carbomer gels of minoxidil by conventional means are hampered by three processing difficulties:

(1) the poor solubility of minoxidil;
(2) difficulties in obtaining effective and efficient carbomer dispersion and maintenance of polymer solution; and
(3) precipitation of a drug-carbomer complex.

Surprisingly and unexpectedly, the method of the instant invention produces a pharmaceutically acceptable gel containing minoxidil which is pharmaceutically elegant and avoids the three problems noted above.

Conventional carbomer gel formulations involve the sequential mixing of a solvent, a polymer, and a neutralizing agent. The drug is added before the neutralizing agent is added. This sequence is generally preferred in the preparation of gels.

However, minoxidil cannot be formulated into a carbomer gel by such conventional means. Addition of the components in the conventional manner leads to the formation of a white precipitate which is believed to be a minoxidil-carbomer complex. Isolation and analysis of the precipitate indicates the presence of both carbomer and minoxidil.

By "pharmaceutically acceptable glycol" is meant glycol which is non-toxic, and does not irritate the skin at the concentrations of this invention. Suitable glycols include propylene glycol, 1,3-butylene glycol, propylene glycol 200 (PEG 200), polyethylene glycol 400 (PEG 400) hexylene glycol, and dipropylene glycol. Propylene glycol is preferred.

The process used to prepare the gel of the instant invention proceeds as follows:

Three components are prepared separately and are mixed as described below. Part I contains carbomer (described in National Formulary (NF)XV at p. 1216 (1980 ed) and commercially available as Carbopol ®) and water (preferably purified). This part may be prepared directly from carbomer and water or from a previously prepared dispersion. A second part is prepared containing minoxidil from greater than 0 to 5% on a weight-to-weight basis; propylene glycol and/or 1,3-butylene glycol (1,3-butane diol), and/or other suitable glycol in an amount approximately 10 times that of the minoxidil for propylene glycol or an equivalent saturated amount for other glycols; an alcohol (ethanol or isopropanol) in the range of 12.9 to 30% and an amine which is both water and alcohol soluble, such as diisopropanolamine (DIPA), triisopropanolamine, trolamine (triethanolamine), monoethanolamine or a polyamine such as Quadrol. DIPA, ethanol, and propylene glycol are preferred. The amine should be present in the mixture in the range from about 0.25 to about 1.5%. A third part is prepared containing the above-described alcohol in the range of 27.1 to 5%. A small amount of the amine may also be present in this third part, i.e., up to 0.4% on a weight-to-weight basis. However, it is preferred that no amine be present in Part III. All percents are expressed on a weight-to-weight basis.

Part III is then mixed with Part I by conventional means. After a uniform mixture is obtained, Part II is then added. A planetary mixing action under vacuum is preferred.

Surprisingly and unexpectedly it has been found that this sequence of addition produces a pharmaceutically elegant gel which is not obtainable by conventional means. If the components are added in the conventional manner a white precipitate forms. The key element is the mixture of the amine with the minoxidil in Part II. The process precipitation problem is thus avoided. The preparation of Parts I and III provide for a processible carbomer dispersion and helps to maintain the polymer solution, thereby insuring acceptable gel viscosity and clarity.

In order to produce and maintain drug solubility in the preparation of Part II, the ratio of drug to the propylene glycol must be on the order of approximately 1 to 10 or an equivalent saturated amount for other glycols. A minimum amount of alcohol, determined by total drug concentration, is also required. If the minoxidil is not added simultaneously with the diisopropanolamine (DIPA) or similar amine to the carbomer dispersion, a stringy white precipitate forms. Thus, the addition of the DIPA or similar amine to Part II effectively "masks" the minoxidil and carbopol in such a way that these otherwise incompatable ingredients can be combined without difficulty.

A gel prepared using this process rather than conventional means avoids the problem of poor minoxidil solubility, allows the combination of otherwise incompatible ingredients, and facilitates carbomer dispersion manufacture.

A maximum concentration of alcohol of approximately 40% is preferred for satisfactory gels. This amount of alcohol is preferred to maintain fluidity of the Part I dispersion, since at higher minoxidil concentrations which necessitate a higher glycol content, further reductions in the fluid volume of Part I would result in a non-uniform, "doughy" mass during processing. An alternate reason for limiting the formulation alcohol to 40% is that the gel viscosity is reduced and hazing is increased in response to the carbomer's reaction to an unfavorable, potentially unstable, solvent environment.

Suitable colorants, perfumes, or similar pharmaceutical excipients may be added to the gel to obtain pharmaceutical elegance.

Surprisingly and unexpectedly it has been found that the formulation parameters described herein produce a gel with clarity and acceptable viscosity.

Minoxidil is well known and may be prepared by known means, e.g., as disclosed in U.S. Pat. No. 3,461,461, which is expressly incorporated by reference herein. The minoxidil gels of the instant invention may be used as described in U.S. Pat. No. 4,139,619, which is also expressly incorporated by reference herein.

DESCRIPTION OF THE PREFERRED EMBODIMENTS

The present invention is seen more fully by the Examples given below.

EXAMPLE 1

Preparation of minoxidil gels.

Pharmaceutically elegant 1, 2, and 3% minoxidil gels are prepared by mixing the below-described 3 part mixtures:

|  | % w/w |
|---|---|
| A. Topical minoxidil gel 1% | |
| *Part I* | |
| Purified water USP | q.s. 100 |
| Carbopol ® 934P | 0.45 |
| *Part II* | |
| minoxidil | 1.0 |
| propylene glycol USP | 10 |
| alcohol USP | 13 |
| diisopropanolamine NF | 0.45 |
| *Part III* | |
| alcohol USP | 27 |
| B. Topical minoxidil gel 2% | |
| *Part I* | |
| purified water USP | q.s. 100 |
| carbopol 934P | 0.5 |
| *Part II* | |
| propylene glycol USP | 20 |
| alcohol USP | 13 |
| minoxidil | 2 |
| diisopropanolamine NF | 0.5 |
| *Part III* | |
| alcohol USP | 27 |
| C. Topical minoxdil gel 3% | |
| *Part I* | |
| purified water USP | q.s. 100 |
| carbopol 934P | 0.5 |
| *Part II* | |
| minoxidil | 3.0 |
| propylene glycol U.S.P. | 30 |
| alcohol USP | 13 |
| diisopropanolamine NF | 0.5 |
| *Part III* | |

-continued

| % w/w | |
|---|---|
| alcohol USP | 27 |

In each of the above cases, the component parts are prepared separately. Part III is then mixed with Part I. When a uniform mixture is obtained, Part II is then added using planetary mixing under vacuum until a uniform gel is obtained.

EXAMPLE 2

Topical minoxidil light gel 2%.

82.5 kg of minoxidil gel were prepared as described above using the following quantities in each part:

| % w/w | | Amount |
|---|---|---|
| | Part I | |
| 0.5% | Carbopol ® 934P | 412 g, 500 mg |
| | Purified Water USP | 30 kg, 937 g, 500 mg |
| | Part II | |
| 20% | Propylene Glycol USP | 16 kg, 500 g |
| (2%) | Minoxidil Milled | (1 kg, 650 g)* |
| 13% | Alcohol USP | 10 kg, 725 g |
| 0.5% | Diisopropanolamine NF | 412 g, 500 mg |
| | Alcohol USP q.s. ad if necessary to account for evaporation | 29 kg, 287 g, 500 mg |
| | Part III | |
| 27% | Alcohol USP | 22 kg, 275 g |
| | Alcohol USP q.s. ad | 82 kg, 500 g |

*Calculated by assay.

PREPARATION 1

Aqueous Carbomer Dispersion

A 1.604% Carbomer dispersion was prepared by mixing the following ingredients:

| | Amount |
|---|---|
| Purified water, USP | 73 kg |
| Carbopol ® 934P | 1 kg, 203 gm |
| Purified water, USP q.s. ad | 75 kg |

Mixing was performed in a Nauta mixer under vacuum. An opaque, smooth dispersion resulted.

EXAMPLE 3

Minoxidil Gel 2%

A 2% minoxidil gel was prepared by mixing the following 3 parts as described below:

| % w/w | | Kg. | Gm. |
|---|---|---|---|
| | Part I | | |
| | Purified water USP | 6 | 320 |
| 1.604 | Carbopol dispersion (Prep. 1) | 31 | 170 |
| | Part II | | |
| 20 | Propylene glycol USP | 20 | — |

-continued

| % w/w | | Kg. | Gm. |
|---|---|---|---|
| 13 | Alcohol USP | 13 | — |
| 2 | Minoxidil milled Assay 99.4% | 2 | 012 |
| 0.5 | DIPA | — | 500 |
| | Part III | | |
| 27 | Alcohol USP | 27 | — |
| | Alcohol USP qs ad | 100 | — |

Parts I and III were mixed in a Nauta mixer under vacuum. When a uniform mixture was obtained, the Part II component was added, and mixing was continued under vacuum until a uniform gel was obtained. The product had a pH of 8.04, and a viscosity of 7980 centipoise at a shear rate of 7.61 sec$^{-1}$.

I claim:

1. A pharmaceutically-acceptable gel composition comprising the following components:

| Component | Amount (% w/w) |
|---|---|
| (a) water | q.s. 100 |
| (b) carbomer | 0.25-1.5 |
| (c) minoxidil | 0.001-3 |
| (d) pharmaceutically-accetable glycol | 0.01-30 |
| (e) ethanol or isopropanol | 20-40 |
| (f) a water and alcohol-soluble amine | 0.25-1.5 | wherein the ratio of minoxidil to the glycol is sufficient for a saturated solution of minoxidil.

2. A gel of claim 1, wherein the amine is diisopropanolamine (DIPA), the alcohol is ethanol, the water is purified, and the glycol is propylene glycol.

3. A gel of claim 2, wherein the amount of minoxidil is 1.0%, the amount of carbomer is 0.45%, the amount of propylene glycol is 10%, the amount of ethanol is 40%, and the amount of DIPA is 0.45%.

4. A gel of claim 2, wherein the amount of minoxidil is 2.0%, the amount of carbomer is 0.5%, the amount of propylene glycol is 20%, the amount of ethanol is 40%, and the amount of DIPA is 0.5%.

5. A gel of claim 2, wherein the amount of minoxidil is 3%, the amount of carbomer is 0.5%, the amount of propylene glycol is 30%, the amount of ethanol is 40%, and the amount of DIPA is 0.5%.

6. A gel of any preceding claim, wherein the carbomer has a molecular weight approximately $3 \times 10^6$.

7. A process for preparing a gel of any preceding claim, which comprises a first step of mixing the water, the carbomer, 5 to 27.1% w/w of the alcohol, and 0 to 0.04% w/w of the amine; and a subsequent second step of mixing, until a uniform gel is obtained, the mixture of the first step with the minoxidil, the glycol, 12.9 to 30% w/w of the alcohol, and the or the remainder of the amine; the percentages being with respect to the total composition.

8. A process of claim 7, wherein no amine is present in the first step.

9. A process of claim 8, for preparing a gel of claims 4 or 5, wherein the first step comprises mixing the water, a carbomer of approximate molecular weight of $3 \times 10^6$ and 27% w/w of the ethanol.

* * * * *